United States Patent [19]

Robinson et al.

[11] Patent Number: 5,116,602
[45] Date of Patent: May 26, 1992

[54] ANTIPLAQUE ORAL COMPOSITIONS

[75] Inventors: Richard S. Robinson, Piscataway, N.J.; Arthur B. Buzin, Jamison, Pa.; Ruby E. Kirkup, Bridgewater, N.J.

[73] Assignee: Colgate-Palmolive Company, Piscataway, N.J.

[21] Appl. No.: 413,366

[22] Filed: Sep. 27, 1989

[51] Int. Cl.$^5$ ............................................. A61K 7/16
[52] U.S. Cl. ........................................ 424/49; 424/48
[58] Field of Search ............................ 424/49–58

[56] References Cited

U.S. PATENT DOCUMENTS

| | | | |
|---|---|---|---|
| 4,294,894 | 10/1981 | Velluci | 424/49 |
| 4,310,705 | 1/1982 | Nissen et al. | 568/391 |
| 4,446,125 | 5/1984 | Mookherjee et al. | 424/49 |
| 4,562,064 | 12/1985 | Steltenkam et al. | 424/49 |
| 4,844,886 | 7/1989 | Hartmann et al. | 424/62 |
| 4,891,447 | 1/1990 | Eilerman et al. | 568/496 |

FOREIGN PATENT DOCUMENTS 58-213706A 12/1983 Japan ............................ 424/58
1429774 3/1976 United Kingdom .

OTHER PUBLICATIONS

Mookherjee et al. C.A.101 #109307k of U.S. 4446125 May 1, 1984 nerolidol in toothpaste.
Lion Corp. CA.100 #126742r of JP 58213706 Dec. 12, 1983 bisabolol antiplaque oralon.
Dragoro CA. 87 #90573n of Dragoco Rep 24(4):7981,84–92 (1977) a bisabolol in mouth washes.
Metz et al. CA. 84 #155665d of Ger. Offen DE 2426343 Dec. 4, 1975 a bisobolol in gargle mouthwash.

*Primary Examiner*—Shep K. Rose
*Attorney, Agent, or Firm*—Robert L. Stone; Murray M. Grill

[57] ABSTRACT

An antiplaque oral composition containing a low concentration of a sesquiterpene alcohol flavor compound to inhibit the formation of dental plaque in the presence of an additive selected from the group consisting of benzoic acid, a preservative, and a polycarboxylate and mixtures thereof, in an oral vehicle having a low pH of about 3-5.

10 Claims, 1 Drawing Sheet

A - Farnesol + 0.10% Propylparaben
B - Farnesol + 0.10% Dehydroacetic acid
C - Farnesol + 0.13% Gantrez S-97
D - Farnesol + 0.10% Benzoic acid
E - pH vs Farnesol Antimicrobial Activity (without preservatives)

ANTIPLAQUE ORAL COMPOSITIONS

The present invention relates to novel oral antiplaque products including mouthwashes, mouthrinse concentrates, dentifrice, lozenges, chewing gums, dental floss and the like, having a low acid pH, comprising a sesquiterpene alcohol flavor compound combined with at least one of benzoic acid or preservative or a polycarboxylate to inhibit the formation of dental plaque.

BACKGROUND OF THE INVENTION

Dental plaque is a film of bacteria which adheres to teeth. It is established that there is a relationship between dental plaque and gingivitis. Due to the inadequacy of mechanical removal of plaque via toothbrushing, there is much interest in chemical inhibition of plaque formation.

The prior art has disclosed the use of cationic antimicrobials such as chlorohexidine, cetyl pyridinium chloride, sanguinarine chloride and the like in oral compositions to reduce dental plaque and gingivitis. The efficacy of the cationics is believed to be due to their substantivity to oral surfaces and their slow release over a long period of time. However, an inherent problem in formulating cationics into oral formulations is their incompatibility with anionic ingredients such as surfactants, fluoride, and sweeteners. Other problems associated with the cationics include the staining of oral surfaces, and bitter after-taste.

The prior art has also disclosed the use of essential oils such as thymol, methyl salicylate and eucalyptol in a hydro-alcoholic mouthrinse vehicle, to reduce plaque and gingivitis, in the *Journal of Clinical Periodontology* 1987; 14:285-288; *Clinical Preventive Dentistry*, Vol. 5, No. 6, November-December 1983; *Journal of Clinical Periodontology* 1985:12:697-704; and *Journal of Dent. Res.* 65:274(Abstract 941), 1986. The efficacy of these compounds is thought to be related to their antiseptic properties. However, mouthrinses formulated with these compounds are characterized by a strong, unpleasant taste.

Also disclosed in the prior art is the bacteriostatic activity of some Australian essential oils such as sandalwood oil containing farnesol and santalol, in an article by Beylier in *Perfumer and Flavorist*, 4 (April-May), 1979, pp. 23-25. Since the bacteriostatic activity of Australian Sandalwood oil exhibits inhibition of growth of the test organism *Staphylococcus aureus*, it was suggested that sandalwood oil could be formulated into cosmetics such as creams, lotions, deodorants, shampoos, and bath oils, for its antiseptic activity.

DE Patent Disclosure No. 3,315,058 (June 13, 1985) by Brunke et al discloses synthetic farnesol, synthetic farnesol mixtures, and isomers of farnesol which can be used as bacteriostatics in cosmetic products for the protection and care of the human skin, particularly in a deodorant pump spray or deodorant stick. Discernable antibacterial action against the tested bacterial species *Staphylococcus epidermis*, *Staphylococcus aureus* and *Cornebacterium* species exhibited the prevention of body odor.

An article by Brunke, E. J., Jellinek, J. S. and Koester, F. W., in *Pollena-TSPK*, 5-8/86 XXX, pp. 151-155, discloses that four stereoisomers of farnesol have bacteriostatic activity against various bacterial cultures in vitro, and stereoisomers of bisabolol possess anti-inflammatory activity in rabbits.

U.S. Pat. No. 4,214,909 discloses sesquiterpene alcohols such as farnesol, nerolidol, and organic esters thereof as anti-fouling agents for controlling aquatic organisms such as algae, barnacles, seaweed, slime, etc.

U.S. Pat. No. 4,775,534 discloses a miticidal composition against spider mites comprising farnesol and/or nerolidol impregnated into a controlled release substrate in solid or liquid form. Said solid substrates are porous particulates such as silica, talc, clay, gelatin and gels, polymers, nylon, cellulose, finely ground corn cobs and the like. Liquid forms of said controlled release substrate include vegetable and/or mineral oils, preferably containing surfactants, wetting agents, emulsifying agents, dispersing agents and the like. The farnesol and/or the nerolidol functions as behavior or modifying chemicals for attracting spider mites, thereby reducing their population.

None of the above cited prior art discloses an oral antiplaque product containing low concentrations of a sesquiterpene alcohol flavor compound as the antiplaque agent in the presence of at least one of benzoic acid, preservative, or a polymeric polycarboxylate in an oral vehicle having a low pH of about 3 to 5.

SUMMARY OF THE INVENTION

It has now been found that oral antiplaque compositions containing very low concentrations of sesquiterpene alcohols in the presence of benzoic acid, preservative, an anionic linear polymeric polycarboxylate, or an anionic crosslinked polycarboxylate, in an oral vehicle having a low pH, can provide significant antimicrobial activity against human oral dental plaque producing bacteria.

Accordingly, a primary object of this invention is to provide an oral antiplaque product containing an antiplaque sesquiterpene alcohol flavor compound having antimicrobial activity at low concentrations.

Another object of the present invention is to provide an oral product containing a sesquiterpene alcohol flavor component selected from the group consisting of farnesol, nerolidol, bisabolol and santalol (sandalwood oil) to inhibit the formation of dental plaque in the presence of benzoic acid and at a low pH.

Still another object of the present invention is to provide an oral antiplaque non-staining product containing a sesquiterpene alcohol antiplaque agent having a pleasant taste and compatible with anionic components in the oral formulation.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel antiplaque oral product of this invention has enhanced antimicrobial properties and contains as the essential antiplaque agent a low concentration of a sesquiterpene alcohol flavor compound in the presence of benzoic acid, a preservative, a polymeric linear or crosslinked carboxylate, or a combination thereof, in an oral vehicle having a low pH of about 3-5 and preferably 3-4.

More specifically, the non-staining pleasant tasting antiplaque oral composition comprises as the essential antiplaque agent a sesquiterpene alcohol selected from the group consisting of farnesol, nerolidol, bisabolol and santalol in an amount of about 0.05 to 1.0% by weight, in the presence of about 0.1% to 2.0% by weight of at least one additive selected from the group consisting of benzoic acid, organic preservative, and a polymeric carboxylate, in a dental vehicle having a pH of about 3 to 5.0, preferably 3-4.

The oral composition may be in the form of a mouthwash or rinse, dentifrice, lozenge, chewing gum and dental floss.

DETAILED DESCRIPTION OF THE INVENTION

Figure 1:
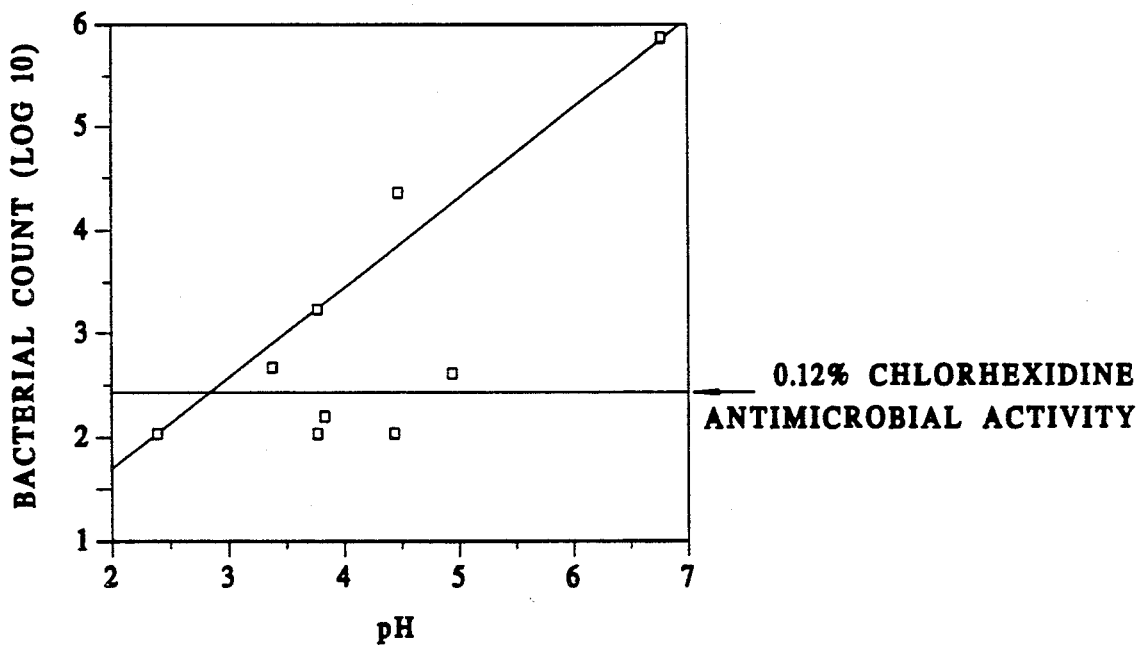

It has been unexpectedly found that sesquiterpene alcohol flavor compounds such as farnesol, nerolidol, bisabolol and santalol, formulated into oral compositions such as mouthrinses, dentifrices, and the like, provide antimicrobial activity at very low concentrations. These flavor compounds are different from commonly used phenolics such as thymol, in that they show antimicrobial activity at lower concentrations, have lower toxicity and less objectionable taste. The sesquiterpene alcohols have the advantages of compatibility with anionic components in the formulation, better taste and lower toxicity.

It has also been found that antibacterial activity of the sesquiterpene alcohol is increased in the presence of benzoic acid, in the oral formulation having a low pH. The addition of components which raise pH, such as pyrophosphate and sodium benzoate, result in reduced antibacterial activity.

It has additionally been found that the addition of an organic preservative or a polymeric carboxylate to a sesquiterpene alcohol-containing oral composition having a low pH of about 3 to 5, exhibits increased antimicrobial activity and superior antiplaque activity. Suitable preservatives include propyl-paraben, (propyl-parahydroxy benzoate), methyl paraben, dehydroacetic acid, sorbic acid, and the like, in amounts of about 0.1 to 2.0% by weight.

The polymeric carboxylates utilized in present invention in amounts of about 0.1 to 2% by weight are anionic linear or crosslinked polymeric polycarboxylates having a molecular weight of about 1,000 to about 1,000,000, preferably in the form of water soluble alkali metal (potassium and sodium) or ammonium salts. The linear polycarboxylates are preferably 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), A.N. 119 (M.W. 250,000) and preferably S-97 Pharmaceutical Grade (M.W. 70,000), of GAF Corporation. Other linear polymeric polycarboxylates include 1:1 copolymers of maleic anhydride with ethyl acrylate, hydroxyethyl methacrylate or methyl vinyl ether; 1:1 copolymers of acrylic acid with methyl or hydroxyethyl methacrylate, methyl or ethyl acrylate, iso-butyl vinyl ether or N-vinyl-2-pyrrolidore; copolymers of maleic anhydride with styrene, isobutylene or ethyl vinyl ether, polyacrylic, polyitaconic and polymaleic acids, and sulfoacrylic oligomers. The copolymers contain sufficient carboxylic salt groups for water-solubility.

The crosslinked polycarboxylates are preferably carboxyvinyl polymers made by B. F. Goodrich and designated by the trademarks Carbopol 934, Carbopol 940 and Carbopol 941. Each of these products consist essentially of a colloidally water soluble polymer of acrylic acid crosslinked with about 0.75 to 2.0% of a crosslinking agent selected from the class consisting of pollyalkyl sucrose and polyyalkyl pentaerythritol.

Combinations of preservatives and Gantrez can also be used as additives for the sesquiterpene alcohol flavor compounds. Likewise, benzoic acid can be combined with preservatives such as parabens or dehydroacetic acid.

In one study using the SIKT test, farnesol rinses without benzoic acid were formulated and adjusted to pH 3, 4, 5 and 6 with dilute HCl. The results in Table I demonstrate no antibacterial activity at these pHs.

The SIKT test is a basic microbiological test which incorporates a fixed contact time. 1 ml of dentifrice or rinse solution is mixed with a pre-determined inoculum of Actinomyces viscosus T14V (between $1 \times 10^6$ to $1 \times 10^7$ cfu/ml) for a 60 second contact time. The system is then neutralized to inhibit further antimicrobial activity. The surviving bacteria are enumerated using plate count methodology. The reduction in counts compared to a water control is the basis for expressing activity. A three log reduction is usually considered significant.

TABLE 1

| SIKT[1] Investigation of Farnesol/pH Range* | | |
|---|---|---|
| Sample | Bacterial Count (CFU/ml) Log 10[2] | % Reduction |
| 1. 0.05% Farnesol/pH 6.23 | 6.86 | 0 |
| 2. 0.05% Farnesol/pH 5.30 | 6.91 | 0 |
| 3. 0.05% Farnesol/pH 4.19 | 6.92 | 0 |
| 4. 0.05% Farnesol/pH 3.11 | 6.20 | 0 |

*Rinses formulated without benzoic acid.
[1]Short interval killing time.
[2]Colony forming units of viable bacteria/ml.

Farnesol rinses without benzoic acid at various pHs showed a lack of antibacterial activity with farnesol alone even at low pH. However, further analysis of these samples revealed that they were not sufficiently buffered to keep the pH stable after dilution with phosphate buffer. It has been found that incorporating acids such as citric, ascorbic or phosphoric have sufficient buffer capacity to keep the pH after dilution between 3 and 4.

Accordingly, sufficiently buffered farnesol rinses, to keep the low pH stable after dilution with a phosphate buffer, exhibit antimicrobial activity in vitro as disclosed in Table II.

TABLE II

| SIKT Testing of pH vs Farnesol Activity | | | | |
|---|---|---|---|---|
| Sample | pH as is | pH (tested)* | Bacterial Count** | % Reduction |
| 1. 0.05% Farnesol | 2.12 | 2.41 | 2.00 | >99.99 |
| 2. 0.05% Farnesol | 3.18 | 3.40 | 2.65 | >99.99 |
| 3. 0.05% Farnesol | 3.34 | 3.79 | 3.18 | >99.90 |
| 4. 0.05% Farnesol | 3.06 | 4.47 | 4.38 | >99.00 |
| 5. 0.05% Farnesol | 4.07 | 6.76 | 5.90 | 0 |

*After 1:1 dilution with phosphate buffer containing bacterial cells (pH-7).
**Bacterial count log 10.

In a second study, farnesol rinses containing benzoic acid were formulated at three different pHs, 3, 5 and 6. The results in Table III confirm the antibacterial activity of farnesol in the presence of benzoic acid and at a low pH (Sample 3).

TABLE III

SIKT Investigation of Farnesol/pH Range with Benzoic Acid

| Sample | Bacterial Count (CFU/ml) Log $10^2$ | % Reduction |
|---|---|---|
| 1. 0.05% Farnesol/pH 6.10 | 7.08 | 0 |
| 2. 0.05% Farnesol/pH 5.05 | 7.04 | 0 |
| 3. 0.05% Farnesol/pH 3.15 | 2.88 | >99.99 |
| 4. Placebo (0.1% benzoic acid/pH 3.20) | 6.95 | 0 |

These results suggest a synergistic relationship between farnesol and benzoic acid, at an acid pH of 3.15 (Sample 3).

The sesquiterpene alcohol compound constitutes about 0.05 to 1.0% by weight of the oral composition. The benzoic acid ingredient constitutes about 0.1 to 2.0% by weight of the oral composition.

The synergistic mixture of farnesol and benzoic acid in an acid medium having a pH of about 3 to about 5 in an oral composition exhibits superior antiplaque activity in vivo as disclosed in Table IV. A procedure for measuring the amount of plaque growth on human teeth after 24 hours was used as a screening test to examine the antiplaque mouthrinses. Human panelists clean their teeth with thorough toothbrushing with an inert dentifrice. The remaining plaque is disclosed and photographed for scoring (obtaining a 0 hr. score). The test rinse is used for 30 seconds, after which no oral hygiene is permitted for 24 hours. After 24 hours, the plaque growth is disclosed, photographed and scored (obtaining a 24 hr. score). Subtraction of the 0 hr. score from the 24 hr. score results in the 24 hr. plaque growth score. This procedure is repeated four days consecutively (Monday through Friday) to get four 24 hr. plaque growth scores per panelist for each test product. A three day wash-out period over the weekend prevents carry-over effects on the next test product. Results of this screening test have been shown to correlate to longer-term clinical plaque studies.

The farnesol mouthrinse was tested against a placebo rinse and commercially available products containing 0.26% essential oils such as thymol, menthol, methyl salicylate, eucalyptol, 0.03% sanguinaria extract, and 0.05% cetyl pyridinium chloride.

TABLE IV

24 Hour Plaque Scores of Antimicrobial Mouthrinses

| Dentifrice | 24 Hour Plaque Score | % Reduction vs Placebo |
|---|---|---|
| Placebo (hydroalcoholic vehicle) | 44.68 ± 5.18* | — |
| Essential oils mouthrinse | 18.67 ± 3.57 | 58.2 |
| Sanguinaria extract mouthrinse | 22.90 ± 5.61 | 48.7 |
| 0.05% Cetyl pyridinium chloride mouthrinse | 34.54 ± 5.11 | 22.7 |
| 0.08% Farnesol mouthrinse (Example 1) | 17.60 ± 3.13 | 60.6 |

*Standard error of the mean

The results show that the 0.08% farnesol mouthrinse (Example 1) has excellent antiplaque activity compared to commercially available products, i.e. sanguinaria extract mouthrinse and the essential oils mouthrinse, significantly higher antiplaque activity than the placebo, and the cetyl pyridinium chloride mouthrinse. It is also noted that the amount of 0.26% essential oils in the said mouthrinse is over three times greater than the 0.08% farnesol mouthrinse.

The synergistic mixture of farnesol and preservatives or Gantrez in an acid medium having a low pH of 3 to 5 also exhibits greater antimicrobial activity in vitro than farnesol at a low pH alone as disclosed in Table V and FIG. 1.

TABLE V

SIKT Antimicrobial Activity of Farnesol + Preservatives/Gantrez vs pH

| Sample | pH as is | pH (tested)* | Bacterial Count** | % Reduction |
|---|---|---|---|---|
| A. 0.05% Farnesol/ | 3.19 | 4.97 | 2.00 | >99.99 |
| 0.10% Propylparaben | 6.05 | 6.89 | 4.63 | 99.00 |
| B. 0.05% Farnesol/ | 3.65 | 4.46 | <2.00 | >99.99 |
| 0.10% Dehydroacetic acid | 6.21 | 7.02 | 5.51 | 90.00 |
| C. 0.05% Farnesol/ | 3.22 | 3.85 | 2.18 | >99.99 |
| 0.13% Gantrez S-97 | | | | |
| D. 0.05% Farnesol/ | 3.42 | 3.80 | 2.00 | >99.99 |
| 0.10% Benzoic acid | 6.10 | 6.98 | 7.08 | 0 |

*After 1:1 dilution with phosphate buffer containing bacterial cells (pH-7).
**Bacterial count log 10.

The synergistic mixture of farnesol and Carbopol in an acid medium also exhibits greater antimicrobial activity in vitro than farnesol alone, at a low pH, as disclosed in Table VI.

TABLE VI

In Vitro SIKT Testing of Farnesol Rinses Containing Carbopol Polymers

| Sample | Bacterial Count (log 10) | % Reduction |
|---|---|---|
| 0.05% Farnesol | 4.95 | 99.00 |
| 0.05% Farnesol/ 0.20% Carbopol 940 | 4.08 | 99.90 |
| 0.5% Farnesol/ 0.20% Carbopol 934P | 4.11 | 99.90 |
| Chlorhexidine | 4.52 | >99.00 |

In vitro testing of farnesol and other sesquiterpene alcohols demonstrates their antimicrobial activity against a dominant strain of human dental plaque producing bacteria, *Actinomyces viscosus*, in Table VII, using the SIKT test which has been previously described in Table I.

TABLE VII

Short Interval Killing Test (SIKT) against A. viscosus T14V

| Mouthrinse | Bacterial Count (log 10) | % Reduction |
|---|---|---|
| Water | 6.81 | — |
| Placebo (hydroalcoholic vehicle) | 6.74 | — |
| 0.12% chlorhexidine digluconate | <2.00 | >99.9 |
| 0.05% cetyl pyridinium chloride | <2.00 | >99.99 |
| 0.26% essential oils | <2.00 | >99.99 |
| 0.08% farnesol | <2.00 | >99.99 |
| 0.08% sandalwood oil | <2.00 | >99.99 |
| 0.08% nerolidol | <2.00 | >99.99 |
| 0.08% bisabolol | <2.00 | >99.99 |
| 0.09% eucalyptol | 6.85 | — |
| 0.06% methyl salicylate | 6.76 | — |
| 0.07% thymol | <2.00 | >99.99 |

Table VIII compares the in vitro activity of farnesol vs. thymol at different concentrations. The results show that farnesol significantly killed plaque bacteria at one-tenth the effective concentration of thymol.

TABLE VIII

In Vitro Comparison of Farnesol vs Thymol Antimicrobial Activity

| Concentration | Bact. Count (Log 10) | % Red. | Bact. Count (Log 10) | % Red. |
|---|---|---|---|---|
| 0.08 | <2.00 | >99.99 | <2.00 | >99.99 |
| 0.07 | <2.00 | >99.99 | <2.00 | >99.99 |
| 0.06 | <2.00 | >99.99 | 3.93 | 99.99 |
| 0.04 | <2.00 | >99.99 | 6.23 | 0 |
| 0.02 | <2.00 | >99.99 | 6.71 | 0 |
| 0.01 | <2.00 | >99.99 | 6.67 | 0 |
| 0.0075 | 2.50 | >99.99 | ND* | ND |
| 0.005 | 3.66 | 99.9 | ND | ND |

*ND = not determined.

The use of farnesol or other sesquiterpene alcohol in antiplaque oral compositions, in lieu of prior art cationic antimicrobial agents, affords multiple advantages. Farnesol is compatible with anionic surfactants, fluoride and sweeteners. There is no bitter aftertaste nor tooth staining associated with cationic antimicrobials.

In addition, farnesol has advantages over other antimicrobial essential oils such as thymol and eucalyptol in that the sesquiterpene alcohols have a more pleasant taste, and have a lower toxicity as shown in Table IX. The toxicity values are reported in the literature. LD50 is the amount of agent necessary to kill 50% of the test animals.

TABLE IX

Relative Toxicity of Sesquiterpene Alcohols vs. Other Antiseptic Essential Oils

| Compound | LD 50 (Oral, Rat) |
|---|---|
| Farnesol | 6000 mg/kg |
| Sandalwood oil | 3800 mg/kg |
| Nerolidol | >5000 mg/kg |
| Bisabolol | 5000 mg/kg |
| Eucalyptol | 2480 mg/kg |
| Thymol | 980 mg/kg |
| Methyl salicylate | 887 mg/kg |

The antiplaque sesquiterpene alcohol flavor compound may be incorporated into oral compositions generally, such as mouthrinses, mouthrinse concentrates, dentifrices, lozenges, chewing gum or dental floss containing a dental vehicle.

The vehicle, often referred to as a dental vehicle contains liquids and solids in a dentifrice. In general, the liquid comprises water and/or a humectant such as glycerine, sorbitol, propylene glycol or polyethylene glycol including suitable mixtures thereof. It is usually advantageous to use a mixture of both water and one or two humectants. The total liquid content is generally about 20-90 percent by weight of the vehicle. In transparent and translucent vehicles, the liquid content of the toothpaste may be about 20-90 percent by weight, while in opaque vehicles the total liquid content is usually about 20-50 percent by weight. The preferred humectants are glycerine, sorbitol, and polyethylene glycol.

The solid portion of the vehicle is a gelling agent. In the instant invention the gelling agent includes alkali metal carboxymethyl cellulose, hydroxy ethyl cellulose, and hydroxymethyl cellulose in an amount of at least about 0.5 percent by weight of the vehicle. Additional gelling agents may also be present. Gelling agents which may be additionally present include xanthan gum, viscarin, gelatin, starch, glucose, sucrose, polyvinyl pyrollidone, polyvinyl alcohol, gum tragacanth, gum karaya, hydroxy propyl cellulose, methyl cellulose, carboxyethyl cellulose and sodium alginate, Laponite CP or SP, which are each synthetic inorganic complex silicate clays sold under trademark by Laporte Industries, Ltd., and magnesium aluminum silicate gel. The solid portion or gelling agent of the vehicle is typically present in an amount of about 0.5-5 percent by weight of the toothpaste and preferably about 0.5-2 percent by weight.

Any suitable substantially water-insoluble polishing agent may be added to the gel vehicle of the dentifrice. There is a relatively large number of such materials known in the art. Representative materials include, for example, dicalcium phosphate, tricalcium phosphate, aluminum hydroxide, magnesium carbonate, calcium carbonate, calcium pyrophosphate, calcium sulfate, bentonite, alumina, hydrated alumina, aluminum silicate, zirconium silicates, silica, including suitable mixtures thereof. In general, these polishing agents will comprise a major proportion by weight of the solid ingredients. The polishing agent content is variable, but will generally be up to about 75 percent by weight of the total composition, generally about 20-75 percent; although, even lower amounts of polishing agent can be employed.

Any suitable surface-active or detersive material may be incorporated in the gel vehicle. Such compatible materials are desirable to provide detersive and foaming properties depending upon the specific type of surface-active material selected. These detergents are water-soluble organic compounds usually, and may be anionic, non-ionic, or cationic in structure. It is preferred to use the water-soluble non-soap or synthetic organic detergents. Suitable detersive materials are known and include, for example, the water-soluble anionic salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g., sodium dodecyl benzene sulfonate), higher fatty acid esters of 1,2-dihydroxypropane sulfonate) and the like. Other suitable surface active materials include nonionic surface active materials such as condensates of ethylene oxide with propylene oxide condensates of propylene glycol ("Pluronics").

The various surface-active materials may be used in any suitable amount, generally from about 0.05 to about 10 percent by weight, and preferably from about 0.5 to 5 percent by weight of the dentifrice composition.

The oral products of the present invention may also contain antiplaque activity boosters in minimal amounts up to 5% by weight, such as polyvinyl phosphonic acid which deposits on tooth surfaces and inhibits plaque adhesion onto the surface. Farnesol works by a different mechanism: as an antimicrobial it inhibits bacterial reproduction and hence plaque growth. Therefore, the two different mechanisms for fighting plaque could be complementary, showing an additive or even synergistic effect.

The oral products of this invention may also contain conventional ingredients such as coloring or whitening agents such as titanium dioxide, flavoring and/or sweetening materials, fluorides such as sodium fluoride, stannous fluoride and sodium monofluorophosphate. These additional ingredients may each be added to the dentifrice in minimal amounts of up to 5% by weight, and preferably up to 1%, provided they do not interfere with the antiplaque properties of the finished product.

The oral preparation may also be a liquid such as mouth rinse which typically contains 20–99% by weight of an aqueous lower aliphatic alcohol, preferably having about 10–30% by weight alcohol such as ethanol, n-propyl, or isopropyl alcohol, water and, often, about 5–35% humectant.

Such oral preparations are typically applied by brushing the teeth with a dentifrice or toothpaste, or rinsing the oral cavity for 30–90 seconds or in the case of a lozenge, candy or gum, by sucking or chewing in the oral cavity, or in the case of a mouthspray by spraying into contact with oral surfaces at least once daily. Typical oral preparations of the invention which can be applied in this manner are set forth below.

EXAMPLES 1 AND 2

| | Mouthrinse Compositions | |
|---|---|---|
| | Weight Percent | |
| Ingredient | Example 1 (Mouthrinse) | Example 2 (Concentrate)* |
| Deionized Water | 74.330 | 8.580 |
| Ethanol (95%) | 15.000 | 60.000 |
| Glycerine | 10.000 | 30.000 |
| Sodium lauryl sulfate | 0.300 | 0.200 |
| Flavor | 0.160 | 0.400 |
| Benzoic acid | 0.100 | 0.400 |
| Farnesol | 0.080 | 0.320 |
| Sodium saccharin | 0.020 | 0.080 |
| FD & C Blue #1 (1% sol'n) | 0.010 | 0.020 | pH = 3.2
*Dilute 1:4 before use; becomes cloudy at proper dilution.

The mouthrinse is prepared by forming two separate solutions, an ethanol solution containing farnesol, benzoic acid and flavor and an aqueous solution containing sodium lauryl sulfate, glycerin, sodium saccharin and color, combining the two solutions with mixing to complete the mouthrinse.

More specifically, the benzoic acid, farnesol and flavor is dissolved in ethanol and mixed for five minutes. In a separate vessel, the sodium lauryl sulfate and the water is mixed slowly for five minutes. Glycerin, saccharin and color are added to the water solution and mixed about 10 minutes. While mixing the aqueous solution, the alcohol solution is slowly added thereto, and mixed for ten minutes.

The resultant mouthrinse composition is a clear liquid product.

The 0.08% farnesol-containing mouthrinse in the presence of 0.1% benzoic acid and at an acid pH of 3.2 exhibits excellent antiplaque activity compared to prior art antiplaque mouthrinses as shown in Table IV, above.

| Anti-Plaque Mouthrinse | |
|---|---|
| Ingredient | Weight Percent |
| Water | 46.280 |
| 70% Sorbitol | 20.000 |
| 95% Ethanol | 15.000 |
| Glycerin | 15.000 |
| Polyvinyl phosphonic acid | 3.000 |
| Sodium lauryl sulfate | 0.250 |
| Farnesol | 0.160 |
| Pluronic F127[1] | 0.100 |
| Flavor | 0.100 |
| Benzoic acid | 0.100 |
| Sodium saccharin | 0.010 | pH = 3.8
[1]Condensate of ethylene oxide with propylene oxide condensates of propylene glycol.

This mouthrinse is prepared according to the procedure of Example 1 except that the polyvinyl phosphonic acid and the sorbitol is dissolved in the aqueous solution. The Pluronic is dissolved in the ethanol solution.

This antiplaque mouthrinse also exhibits superior antiplaque activity.

EXAMPLE 4

| Anti-Plaque Mouthrinse | |
|---|---|
| Ingredient | Weight Percent |
| Water | 49.270 |
| 70% Sorbitol | 20.000 |
| 95% Ethanol | 15.000 |
| Glycerin | 15.000 |
| Sodium lauryl sulfate | 0.250 |
| Farnesol | 0.160 |
| pluronic F127 | 0.100 |
| Flavor | 0.100 |
| Benzoic acid | 0.100 |
| Sodium saccharin | 0.010 |
| Caramel color | 0.010 | pH = 3.2

This mouthrinse is prepared according to the procedure of Example 3.

This antiplaque mouthrinse also inhibits plaque formation in the oral cavity.

EXAMPLE 5

| Antiplaque Dentifrice Formulation | |
|---|---|
| Ingredient | Weight % |
| 70% Sorbitol | 30.000 |
| Glycerine | 20.000 |
| Water | 18.307 |
| Zeodent 113[1] | 18.000 |
| Sylox 15[2] | 5.500 |
| Sodium lauryl sulfate | 2.500 |
| Farnesol | 1.000 |
| Benzoic acid | 1.000 |
| $H_3PO_4$ | 1.000 |
| Flavor | 0.900 |
| Xanthan gum | 0.850 |
| $TiO_2$ | 0.500 |
| NaF | 0.243 |

-continued

| Antiplaque Dentifrice Formulation | |
|---|---|
| Ingredient | Weight % |
| Sodium saccharin | 0.200 | pH = 4.02
pH (3:1 slurry) = 3.62
[1] abrasive silica supplied by J. W. Huber Co.
[2] thickening silica from W. R. Grace Co.

The dentifrice is prepared by first forming a gel phase by dispersing the xanthan gum in glycerin and mixing for five minutes. The salts (NaF, Na saccharin, benzoic acid and $TiO_2$) are added to the glycerin/xanthan mixture and mixed another five minutes. Sorbitol is slowly added to the mixture and mixed another ten minutes. Water is slowly added, followed by $H_3PO_4$ and mixed ten additional minutes. The resultant gel phase is placed in a mixer to which is added the polishing agent (Zeodent) and the Sylox, and mixed under a vacuum for fifteen minutes at high speed. Sodium lauryl sulfate, flavor and farnesol are added to the mixer and mixed under vacuum for five minutes at a low speed, and recovering the antiplaque dentifrice which is packaged in any suitable container, i.e. tubes, spray cans, etc.

The 1% farnesol-containing dentifrice in the presence of 1.0% benzoic acid at an acid pH of 4.02 exhibits excellent antibacterial activity compared to the dentifrice without farnesol as shown in Table X.

TABLE X

| Data on Dentrifice by MIC (Minimum Inhibitory Concentration) Test Actinomyces viscosus | |
|---|---|
| Sample | MIC (ppm) |
| Dentifrice with 1.0% farnesol | 15.62 |
| Dentifrice without farnesol | >500 |

An effective amount, e.g., about 0.05-0.2% by weight of a sesquiterpene alcohol and about 0.1-2.0% by weight of benzoic acid or other additives such as preservatives, e.g. propylparaben, dehydroacetic acid, etc., and Gantrez is also incorporated in an inert carrier or dissolved in a suitable vehicle in the formulation of chewing gums and lozenges. Gantrez may be replaced by other polycarboxylates. Similarly, the sesquiterpene alcohol and benzoic acid or the other additives are also incorporated into a mouth spray.

EXAMPLES 6 AND 7

| Rinse Formulations with Preservatives & Gantrez | | |
|---|---|---|
| Ingredient | Example 6 Weight % | Example 7 Weight % |
| Water | 47.780 | 47.780 |
| 70% Sorbitol | 20.000 | 20.000 |
| Ethanol 95% | 12.500 | 12.500 |
| Glycerine | 10.000 | 10.000 |
| Propylene glycol | 7.000 | 7.000 |
| Gantrez S97 (liq. ~13%) | 1.920 | 1.920 |
| Sodium lauryl sulfate | 0.250 | 0.250 |
| Dodecylbenzene sulfonate | 0.200 | 0.200 |
| Flavor | 0.120 | 0.120 |
| Propyl paraben | 0.100 | — |
| Dehydroacetic acid | — | 0.100 |
| Farnesol | 0.080 | 0.080 |
| Pluronic F127 | 0.050 | 0.050 | pH = adjust to between 3 and 5.

These rinse formulations exhibit superior antiplaque activity.

A typical lozenge formula contains the following ingredients, in percent by weight, based on the weight of the total formulation:

| 75% to 98% | Sugar |
|---|---|
| 1% to 20% | Corn Syrup |
| .1% to 1% | Flavor oil |
| 0% to .03% | Colorant(s) |
| .1% to 5% | Tableting Lubricant |
| .2% to 2% | Water |
| .05% to 0.2% | Sesquiterpene Alcohol |
| 0.1% to 2.0% | Benzoic Acid |

Sugarless pressed candy may also be formulated to include the synergistic combination of sesquiterpene alcohol and benzoic acid antiplaque agent of this invention. For products of this type, which usually contain powdered sorbitol instead of sugar, synthetic sweeteners are mixed with the powdered sorbitol and flavor(s), colorant(s) and a tablet lubricant are then added. The formula is introduced into a tablet machine to shape the final product. A typical sugarless pressed candy contains the following ingredients, in percent by weight, based on the weight of the total formulation:

| 98% to 99.5% | Sorbitol |
|---|---|
| .1% to .9% | Flavor(s) |
| 0% to .02% | Synthetic Sweeteners |
| 0% to .03% | Colorant(s) |
| .05% to 1% | Tableting Lubricant |
| .05% to 0.27% | Sesquiterpene Alcohol |
| .01% to 2.0% | Benzoic Acid |

Obviously many variations of the above described procedures may be used to prepare pressed candies.

A typical chewing gum may contain the following ingredients, in percent by weight based on the weight of the total gum formulation:

| Ingredients | Weight Percent |
|---|---|
| Gum Base | From about 10% to about 40% |
| Sucrose | From about 50% to about 75% |
| Corn Syrup or Glucose | From about 10% to about 20% |
| Flavor Material | From about 0.4% to about 5% |
| Sesquiterpene Alcohol | From about .05% to about .2% |
| Benzoic Acid | From about 0.1% to about 2.0% |

An alternate chewing gum formulation is as follows:

| Ingredients | Weight Percent |
|---|---|
| Gum Base | From about 10% to about 50% |
| Binder | From about 3% to about 10% |
| Filler (Sorbitol, Mannitol or combination thereof) | From about 5% to about 80% |
| Artificial Sweetener & Flavor | From about 0.1% to about 5% |
| Sesquiterpene Alcohol | From about 0.5% to about .2% |
| Benzoic Acid | From about 0.1% to about 2.0% |

In certain sugarless gums, there is used as the binder ingredient a solution of sorbitol in water containing from about 10% to about 80%, preferably from about 50% to about 75% by weight of sorbitol in $H_2O$. In others, there is used a gum acacia-in-water system containing from about 30% to about 60%, preferably from about 45% to about 50% by weight of gum acacia powder.

The above chewing gum formulations are exemplary only. Many additional formulations are described in the prior art, and in carrying out this invention, such formulations can be employed. It is also possible to prepare an acceptable chewing gum product containing a gum base, flavoring material and a sesquiterpene alcohol-benzoic acid combination according to the teaching of this invention.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutyleneisoprene copolymer, paraffin, petroleum wax, polyethylene, polyisobutylene, polyvinylacetate, etc.; plasticizers such as lanolin, stearic acid, sodium stearate, potassium stearate, etc.

Although this invention has been described with reference to specific examples, it will be apparent to one skilled in the art that various modifications may be made thereto which fall within its scope.

We claim:

1. A mouthrinse comprising farnesol at a concentration of about 0.05 to about 1.0 percent by weight, about 0.1 to 2 percent by weight of at least one additive selected from the group consisting of benzoic acid, an organic preservative, an anionic linear polymeric carboxylate, and an anionic cross-linked polycarboxylate, said mouthwash having a pH of about 3-5.

2. The mouthrinse of claim 1 further comprising an aqueous lower aliphatic alcohol mixture.

3. The composition of claim 2 wherein said mouthrinse contains a humectant.

4. The composition of claim 3 wherein said mouthrinse also contains an anionic surfactant.

5. A method of inhibiting the formation of dental plaque which comprises applying the composition of claim 1 to the oral cavity.

6. The composition of claim 1 wherein said additive is benzoic acid.

7. The composition of claim 1 wherein said additive is propylparaben.

8. The composition of claim 1 wherein said additive is dehydroacetic acid.

9. The composition of claim 1 wherein said additive is methyl vinyl ether-maleic anhydride copolymer.

10. The composition of claim 1 wherein said additive is carboxyvinyl polymer.

* * * * *